(12) United States Patent
Brinker et al.

(10) Patent No.: US 6,948,389 B2
(45) Date of Patent: Sep. 27, 2005

(54) DISSOLUTION TEST SAMPLING

(75) Inventors: Gerald Brinker, North Brunswick, NJ (US); Michael Cai, Old Bridge, NJ (US)

(73) Assignee: Distek, Inc., North Brunswick, NJ (US)

( * ) Notice: Subject to any disclaimer, the term of this patent is extended or adjusted under 35 U.S.C. 154(b) by 100 days.

(21) Appl. No.: 10/392,368

(22) Filed: Mar. 18, 2003

(65) Prior Publication Data

US 2003/0217608 A1 Nov. 27, 2003

Related U.S. Application Data

(60) Provisional application No. 60/365,274, filed on Mar. 18, 2002.

(51) Int. Cl.[7] .......................... G01N 1/14; G01N 35/10; G01N 1/38
(52) U.S. Cl. .................... 73/863.01; 73/863; 73/863.32; 73/864.22; 73/864.34; 436/180
(58) Field of Search ................. 73/863.31–863.32, 73/863, 863.01, 864.25, 864.22, 864.34, 40.5 R; 422/67; 436/50, 180

(56) References Cited

U.S. PATENT DOCUMENTS

| 3,802,782 A | * | 4/1974 | Natelson ............... 73/863.32 X |
| 4,120,661 A | * | 10/1978 | Naono ........................ 422/100 |
| 4,279,860 A | * | 7/1981 | Smolen ........................ 422/63 |
| 4,299,796 A |   | 11/1981 | Hogen Esch ................ 422/63 |
| 4,335,438 A | * | 6/1982 | Smolen ........................ 702/19 |
| 4,578,244 A |   | 3/1986 | Cosgrove, Jr. et al. ....... 422/65 |
| 4,678,639 A |   | 7/1987 | Dong et al. .................... 422/81 |
| 5,055,263 A |   | 10/1991 | Meltzer ........................ 422/65 |
| 5,519,635 A | * | 5/1996 | Miyake et al. .......... 436/180 X |
| 5,589,649 A | * | 12/1996 | Brinker et al. ................ 73/866 |
| 5,849,598 A | * | 12/1998 | Wilson et al. .............. 436/180 |
| 6,231,813 B1 | * | 5/2001 | Ally et al. .............. 436/180 X |
| 6,432,365 B1 | * | 8/2002 | Levin et al. ............ 436/180 X |

FOREIGN PATENT DOCUMENTS

| DE | 4222603 A1 | * | 1/1994 | ............ G01N/1/22 |
| EP | 0 018 092 A1 |  | 10/1980 | ............ G01N/1/00 |
| EP | 206945 A2 | * | 12/1986 | ................ 422/100 |
| EP | 1 164 200 A2 |  | 12/2001 | .......... G01N/33/50 |

* cited by examiner

Primary Examiner—Thomas P. Noland

(57) ABSTRACT

Improved sampler apparatus and methods for dissolution testing include a controller that determines whether several different dissolution testing methods can be performed concurrently by the sampler and controls the sampler in response to the determination; fluid delivery apparatus adapted to pierce a septum and to deliver fluid to or from a collection receptacle through a first aperture, and to permit air flow to or from the collection receptacle through a second aperture; a syringe pump including a distributor having apertures through which fluid flows into and out of the pump chamber, the piston of the syringe pump being moveable adjacent the apertures; and/or a leak sensor responsive to the presence of spilled fluids.

31 Claims, 6 Drawing Sheets

Fig. 10
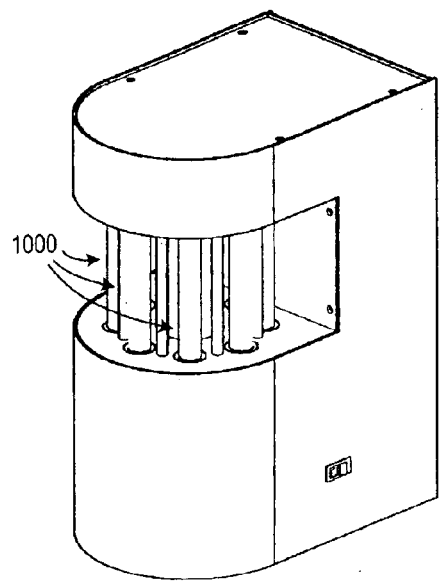
Fig. 12
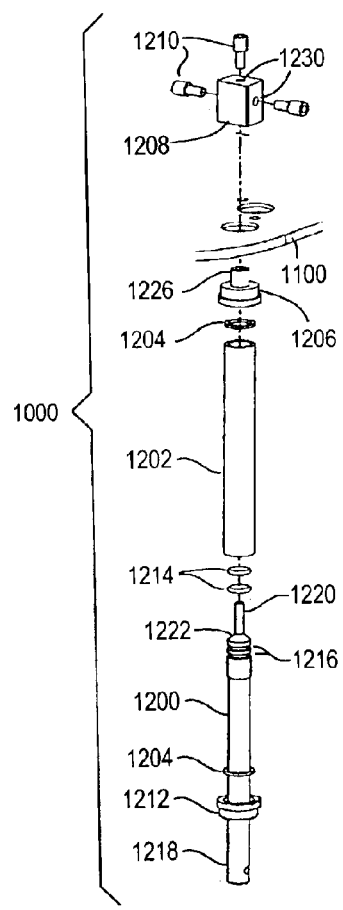
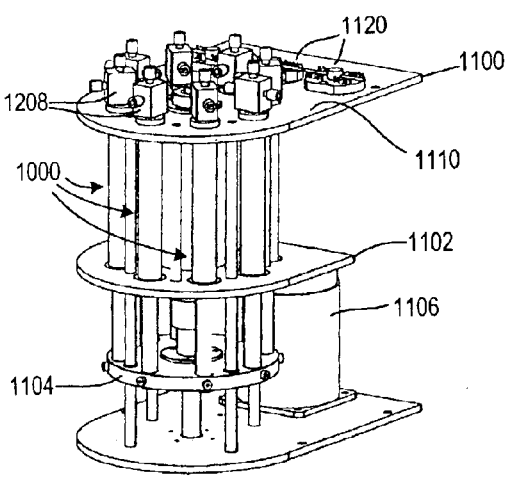
Fig. 11

DISSOLUTION TEST SAMPLING

CROSS-REFERENCE TO RELATED APPLICATIONS

This nonprovisional U.S. national application, filed under 35 U.S.C. § 111(a), claims, under 35 U.S.C. § 119(e)(1), the benefit of the filing date of provisional U.S. national application No. 60/365,274, filed under 35 U.S.C. § 111(b) on Mar. 18, 2002, the teachings of which are incorporated herein by reference.

BACKGROUND OF THE INVENTION

This invention relates to dissolution testing and, in particular, to sampling and sample handling methods and apparatus suitable for use in pharmaceutical product dissolution testing.

Dissolution testing and apparatus for performing such testing are known in the art. U.S. Pat. No. 4,279,860 (Smolen) and U.S. Pat. No. 4,335,438 (Smolen) provide descriptions of the art of dissolution testing. In general, dissolution testing is used to determine the rate of dissolution of a material in a solution. For example, dissolution testing may be used to determine the rate of dissolution of pharmaceuticals in dosage form in specific test solutions to simulate digestion in a human. Requirements for such dissolution testing apparatus are provided in United States Pharmacopeia (USP), Section 711, Dissolution (2000).

Conventional apparatus for dissolution testing of pharmaceutical products includes a dissolution unit having several dissolution vessels, in each of which a test solution and a dosage to be tested, such as a tablet, may be placed. After a dosage to be tested is placed in a test solution in a dissolution vessel, a stirring element in the test solution is rotated at a specified rate for a specified duration. An example of such a dissolution unit is shown in U.S. Pat. No. 5,589,649 to Brinker et al. Samples of the test solution may be withdrawn from the dissolution vessels at various times and delivered to an instrument for analysis to determine the degree of dissolution of the dosages as a function of time.

Dissolution testing of a product typically requires data from a number of dosages of the product, and requires analysis of measured volumes of test solution samples withdrawn at a number of different times for each dosage being tested. Systems commonly referred to as "samplers" have been developed to automate various aspects of the process of withdrawing samples of test solution and conveying the withdrawn samples to an analytic instrument. In such systems, samples and other fluids are conveyed by pumps through tubing lines which are selected by valves. Samplers have been developed which can accommodate testing several (e.g., 6) dosages of a product at the same time, automatically withdrawing samples of test solution from each dissolution vessel at a number (e.g., 19) of specified times. Such samplers automatically deliver withdrawn samples to collection receptacles, such as test tubes or vials, for temporary storage prior to analysis. Samplers may also automatically transfer samples from the collection receptacles to an analytic instrument at an appropriate time for analysis.

Samplers typically include a rack that can hold an array of collection receptacles for storage of collected samples, and a head at which a set of tubing lines terminates, the lines each being connected to a pump which services a particular dissolution vessel. The head and the array of collection receptacles can be relatively moved and positioned with respect to one another so that a particular withdrawn sample can be delivered to a particular collection receptacle for storage. Dissolution testing systems may also include the ability to flush, wash, and purge the tubing lines, and to replace test solution withdrawn from the dissolution vessels with fresh test solution ("media replacement") and/or a portion of the withdrawn test solution that is not delivered to the collection receptacles ("media recycling").

The operation of the pumps and valves and the positioning of the head with respect to the collection receptacles in such a system may be controlled automatically by a programmable controller. Such a controller may be programmed to carry out a predetermined procedure to effect a particular dissolution test method.

Existing samplers have several shortcomings. For instance, they can accommodate only a single dissolution test method at a given time. Also, a collected sample may be stored in a collection receptacle that is capped by a septum, and it can be difficult to deliver a sample to such a collection receptacle. For instance, delivering a sample whose volume is an appreciable fraction of the collection receptacle volume can generate a high pressure in the collection receptacle. Further, fluid leaks and spills may occur in a sampler, which can damage the equipment and can render dissolution test results invalid.

SUMMARY OF THE INVENTION

Problems of the prior art are addressed by improved sampler apparatus and sampling methods. In accordance with embodiments of one aspect of the invention, a controller for a sampler analyzes parameters of several different dissolution test methods to determine whether the test methods can be performed concurrently by the sampler. If not, the controller precludes performing the test methods concurrently, and may generate an output so indicating; if so, the controller controls the sampler to perform the test methods concurrently. In a preferred embodiment of this aspect of the invention, if the controller determines that the test methods cannot be performed concurrently by the sampler, the controller determines whether they could be if certain parameters of the test methods were varied, and if so, controls the sampler to perform the varied test methods concurrently.

In accordance with embodiments of another aspect of the invention, the sampler head includes fluid delivery apparatus adapted to pierce a septum, to deliver fluid to or from the collection receptacle through a first aperture, and to permit air flow to or from the collection receptacle through a second aperture. In a preferred embodiment of this aspect of the invention, the first aperture is within a first tubular needle and the second aperture is within the space between the first needle and a second tubular needle disposed coaxially with and radially outwardly from the first needle.

In accordance with embodiments of another aspect of the invention, the sampler includes a syringe pump, i.e., a pump having a piston that is movable within a cylinder. In a preferred embodiment of this aspect of the invention, the syringe pump includes a distributor having apertures through which fluid flows into and out of the pump chamber, and the piston is moveable adjacent the apertures.

In accordance with embodiments of another aspect of the invention, the sampler includes a leak sensor responsive to the presence of spilled fluids. In a preferred embodiment of this aspect of the invention, the leak detector includes a leak sensor having a pair of conductors that are spaced apart and insulated from each other, and electronic circuitry that is responsive to the electrical properties of the material adjacent the conductors.

BRIEF DESCRIPTION OF THE DRAWINGS

The foregoing and other aspects, features, and advantages of the invention will become more fully apparent from the following detailed description, the appended claims, and the accompanying drawings in which:

FIG. 10 is a perspective illustration of a preferred embodiment of a pump unit in accordance with the invention.

FIG. 11 is a perspective illustration of internal components of the pump unit of FIG. 10.

FIG. 12 is an exploded view of a syringe pump used in the pump unit of FIG. 10.

DETAILED DESCRIPTION

Figure 1:
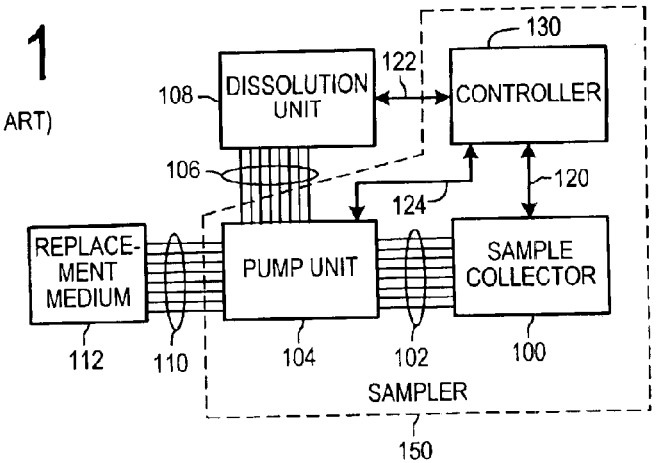
FIG. 1 is a block diagram illustrating elements of a dissolution testing system in accordance with the prior art.

FIG. 1 is a block diagram illustrating elements of a dissolution testing system in accordance with the prior art. The dissolution testing system includes a dissolution unit 108 having a plurality of dissolution vessels, in each of which a test solution and a dosage to be dissolved, such as a tablet, may be placed. The dissolution testing system includes a sampler 150, which includes a pump unit 104, a sample collector 100, and a controller 130. Pump unit 104 includes an array of pumps, not shown, each of which pumps fluid withdrawn from or to be delivered to a particular one of the dissolution vessels.

The pumps in pump unit 104 operate together and pump fluid into or from sets of tubing lines that are selected by valves in pump unit 104. A set of tubing lines 106 is provided, each of which carries fluid between one of the dissolution vessels in dissolution unit 108 and one of the pumps in pump unit 104. A set of tubing lines 102 is provided, each of which carries fluid between one of the pumps in pump unit 104 and one set of a plurality of sets of collection receptacles in sample collector 100. A set of tubing lines 110 is provided, each of which carries fluid between one of the pumps in pump unit 104 and a replacement medium vessel 112 containing a fluid that may be delivered to the dissolution vessels to replace test solution withdrawn during testing.

Controller 130 controls operation of the sampler by signals transmitted between controller 130 and sample collector 100 over communication channel 120 and by signals transmitted between controller 130 and pump unit 104 over communication channel 124. Signals transmitted by controller 130 to pump unit 104 control the pumps and valves; for example, they may cause a sample to be withdrawn from each dissolution vessel and delivered to sample collector 100. Signals transmitted by controller 130 to sample collector 100 control, among other things, which fluid receptacles in sample collector 100 fluid will be delivered to or withdrawn from. For example, they may cause a set of samples withdrawn at a particular time to be delivered to a set of collection receptacles designated to receive samples taken at that time. Signals may also be transmitted between dissolution unit 108 and controller 130 over communication channel 122, for instance, to convey timing signals to cause or communicate the commencement of a test.

In the dissolution testing system of FIG. 1, only one test method can be performed at a time; that is, samples will be withdrawn and handled concurrently and in the same manner for all dosages being tested. In order to perform dissolution testing concurrently on several sets of dosages using a different test method for each dosage set, an entire dissolution testing system as shown in FIG. 1 must be provided for each dosage set.

Figure 2:
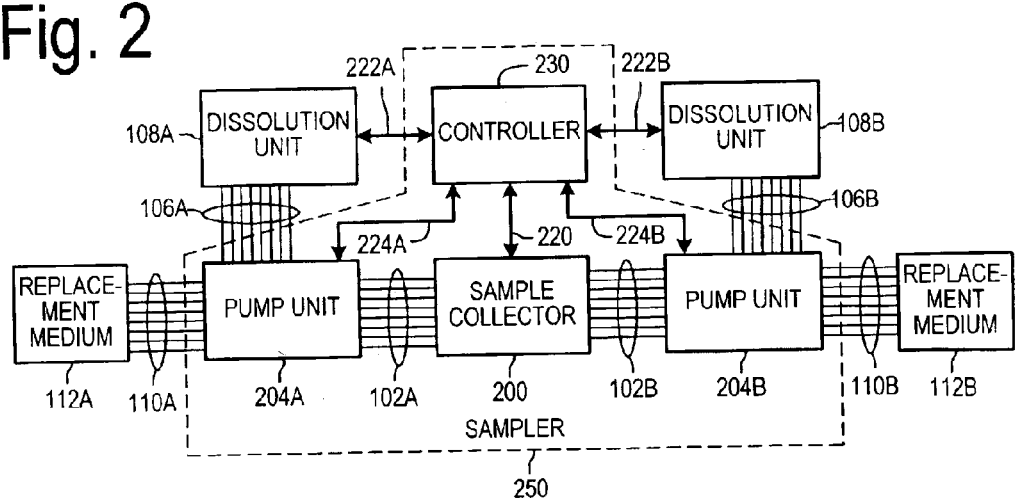
FIG. 2 is a block diagram illustrating elements of a dissolution testing system in accordance with an embodiment of the invention.

FIG. 2 is a block diagram illustrating elements of a dissolution testing system in accordance with an embodiment of the invention. The system of FIG. 2 includes a sampler 250 that enables dissolution testing to be performed concurrently on several sets of dosages using a different test method for each dosage set. A first test method may be used in testing a first set of dosages in dissolution unit 108A serviced by pump unit 204A, and a second test method may be used in testing a second set of dosages in dissolution unit 108B serviced by pump unit 204B. Controller 230 is adapted to control pump unit 204A and pump unit 204B by signals transmitted over communication channels 224A and 224B, respectively. Controller 230 is adapted to control pump unit 204A and pump unit 204B independently, and to enable a test method to be used for the dosages in dissolution unit 108A that is different from the test method to be used for the dosages in dissolution unit 108B. Controller 230 is adapted to control sample collector 200, via signals transmitted over communication channel 220, to deposit samples withdrawn from dissolution unit 108A in a separate set of collection receptacles from those in which samples withdrawn from dissolution unit 108B are deposited. Although for convenience FIG. 2 illustrates separate dissolution units for the different test methods being used, a single dissolution unit could be used it has sufficient dissolution vessels and is compatible with both test methods.

Figure 3:
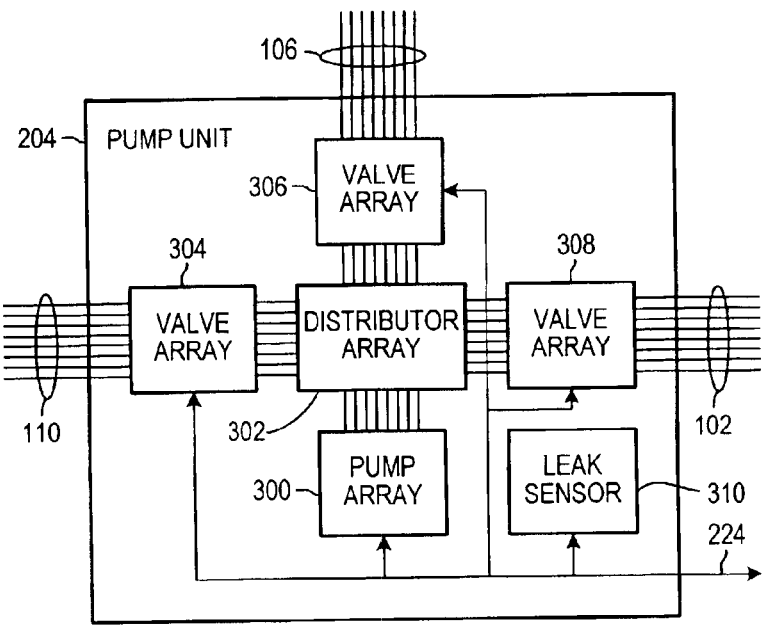
FIG. 3 is a block diagram illustrating elements of a pump unit in accordance with an embodiment of the invention.

FIG. 3 is a block diagram illustrating elements of a pump unit in accordance with an embodiment of the invention. Pump unit 204 includes a pump array 300 connected to a distributor array 302. The distributors in distributor array 302, in the nature of manifolds, are coupled to valve arrays 304, 306, and 308 so as to enable pumped fluid to flow in lines 110, 106, and 102, respectively depending on the valve state as controlled by signals communicated via communication channel 224. Preferably pump unit 204 includes a leak sensor 310.

Figure 4:
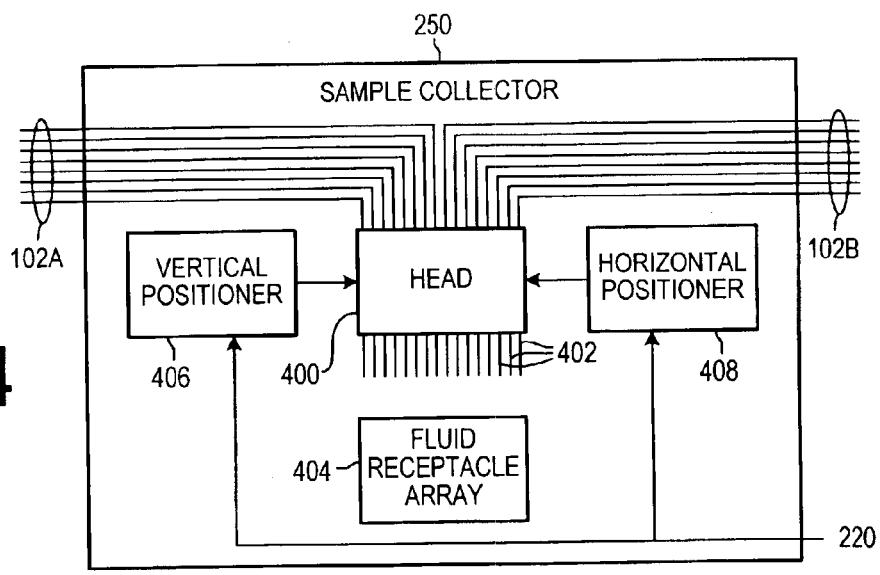
FIG. 4 is a block diagram illustrating elements of a sample collector in accordance with an embodiment of the invention.

FIG. 4 is a block diagram illustrating elements of a sample collector in accordance with an embodiment of the invention. Sample collector 250 includes a fluid receptacle array 404 including an array of collection receptacles. Lines 102 from pump units 204 are terminated at a head 400 where they are coupled to fluid ports 402, typically needles, through which fluid can be withdrawn into or delivered from lines 102. A horizontal positioner 408 relatively positions head 400 and fluid receptacle array 404 horizontally with respect to each other so that fluid withdrawn into or delivered from lines 102 can be withdrawn from or delivered into a desired set of fluid receptacles. A vertical positioner 406 is preferably provided to relatively position fluid ports 402 and fluid receptacle array 404 vertically with respect to each other so that fluid ports 402 may positioned below the surface of fluid in a fluid receptacle and/or so that fluid ports in the nature of needles may pierce and be withdrawn from septa that may be used to cap fluid receptacles. Vertical positioner 406 and horizontal positioner 408 operate under control of signals communicated via communication channel 220.

Figure 5:
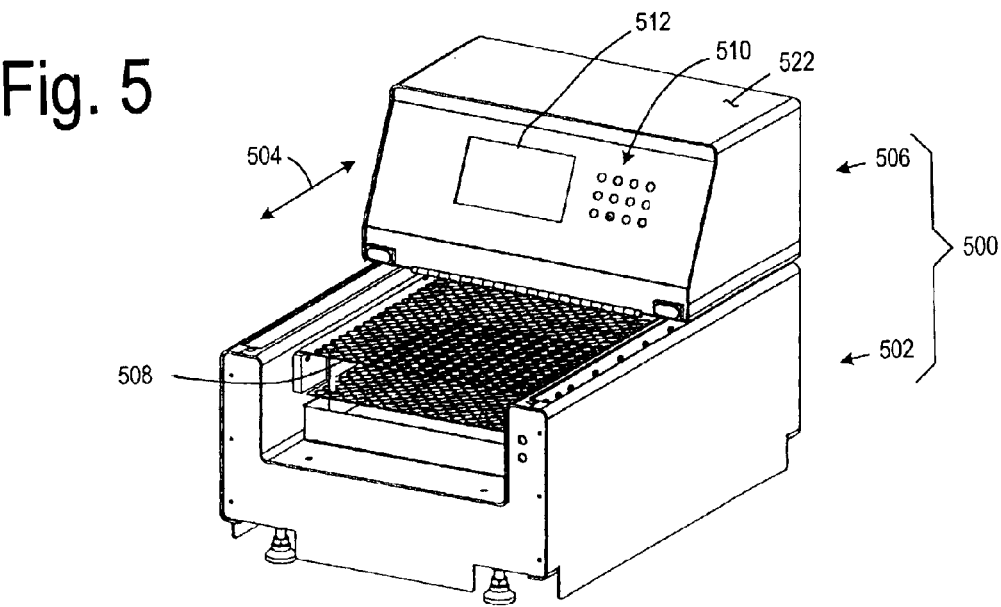
FIG. 5 is a perspective illustration of a preferred embodiment of a sample collector in accordance with the invention.

FIG. 5 is a front, right perspective illustration of a preferred embodiment of a sample collector in accordance with the invention. The sample collector 500 includes a base 502 and a head 506 that is mounted for horizontal movement with respect to base 502 in the direction indicated by arrow 504. The sample collector includes a controller, for which an input device such as keypad 510 and an output device such as display 512 are provided. A horizontal positioning mechanism, which may be based on a conventional mechanism such as a motorized lead screw and located in base 502, positions head 506 with respect to base 502 in accordance with signals from the controller. A rack 508 includes an array of openings to receive collection receptacles such as test tubes or vials. Collection receptacles in a column of the array (i.e., along a line parallel to arrow 504) all receive samples from one dissolution vessel. Samples taken at different times from the dissolution vessel are delivered to different collection receptacles in the row.

Figure 6:
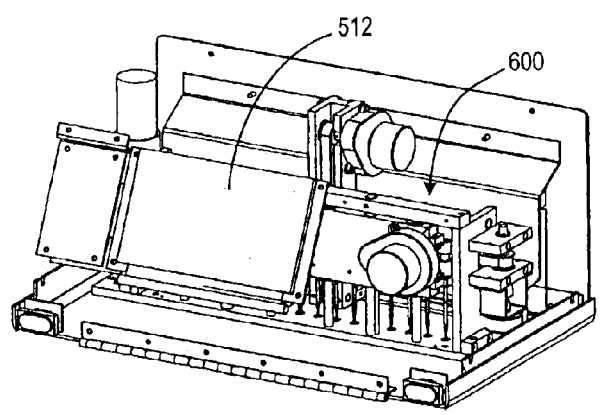
FIG. 6 is a perspective illustration of internal components of the head of the sample collector of FIG. 5.

FIG. 6 is a front, right perspective illustration of head 506 of the sample collector of FIG. 5, shown with head cover 522 removed. Mounted within head 506 is a sampling assembly 600, which is partially obscured by display 512 and is shown in more detail in FIG. 7.

Figure 7:
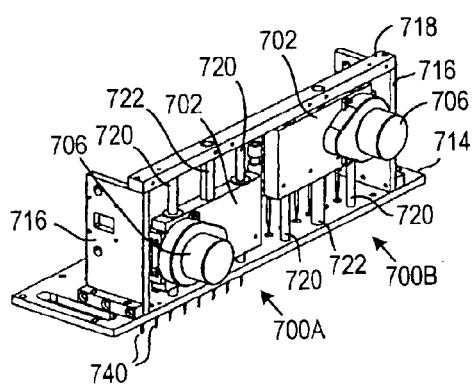
FIG. 7 is a perspective illustration of a sampling assembly used in the head of the sample collector of FIG. 5.
Figure 8:
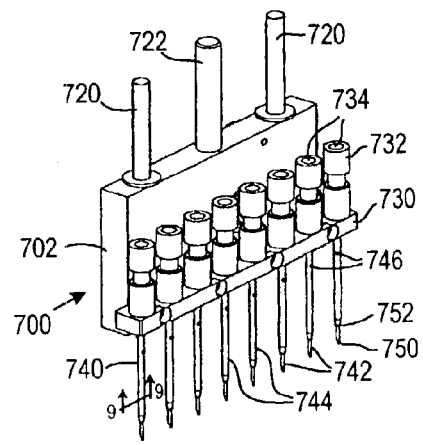
FIG. 8 is a perspective illustration of a needle head used in the sampling assembly of FIG. 7.
Figure 9:
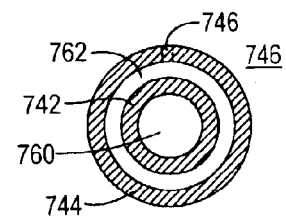
FIG. 9 is an enlarged axial view of a needle used in the sampling assembly of FIG. 7.

FIG. 7 is a front, left perspective illustration of sampling assembly 600. Sampling assembly 600 includes a pair of needle heads 700A and 700B which may be raised and lowered independently, and FIG. 8 is an enlarged rear, right perspective illustration of a needle head 700. Each needle head 700 is mounted for vertical movement on a pair of guide rods 720 that are supported in a frame including plates 714 and 716 and beam 718. Movement of each needle head 700 is provided by a motor 706, mounted to carriage 702, turning a gear that engages a rack 722. A needle holder 730 secured to carriage 702 supports eight needles 740, each of which is coupled to a ferrule 732 adapted to receive a tubing line 102 in an opening 734. Needles 740 act as fluid delivery devices. An enlarged cross-sectional view of a needle 740 taken along the line 9—9 is shown in FIG. 9.

Needle 740 includes a tubular inner needle 742 and a tubular outer needle 744 disposed coaxially with and radially outwardly from inner needle 742. Inner needle 742 and outer needle 744 may, for example, be made from stainless steel hypodermic needle stock of 20 gauge and 16 gauge, respectively. Inner needle 742 and outer needle 744 are adapted to pierce a septum when needle head 700 is lowered, so that the bottom ends 750 and 752 of both needles may be positioned within a capped collection receptacle. The axial space 760 within inner needle 742 communicates with a line 102 via a ferrule 732, provides an aperture through which fluid may be delivered to or withdrawn from a collection receptacle. Delivering fluid into a capped collection receptacle increases the pressure in it, which can be undesirable. The inclusion of outer needle 744 provides a second aperture 762, between the inner surface of outer needle 744 and the outer surface of inner needle 742, in which air can flow to equalize pressure inside and outside a capped collection receptacle when fluid is delivered to or withdrawn from the collection receptacle. Hole 746 in the wall of outer needle 744 is disposed so as to be outside a septum in order to vent air flowing from inside a capped collection receptacle through the space between inner needle 742 and outer needle 744.

Alternatively, instead of a disposing the second needle provided for venting a capped collection receptacle coaxially with the fluid delivery needle, a second needle for venting might be disposed parallel and adjacent to the fluid delivery needle. Mechanical considerations may make that alternative less preferable.

FIG. 10 is a front, right perspective illustration of a preferred embodiment of a pump unit in accordance with the invention, FIG. 11 is a front, right perspective illustration of internal components of the pump unit of FIG. 10, and FIG. 12 is an exploded view of a syringe pump used in the pump array. The pump unit includes a pump array having eight syringe pumps 1000. Syringe pumps 1000 include pistons 1200 and tubular members 1202 having cylindrical inner surfaces which will be referred to as cylinders 1202. The pumps are disposed in the pump unit so that movement of their pistons 1200 within their cylinders 1202, which preferably are made of glass, may be visible. Pistons 1200 are preferably made of Teflon®. Syringe pumps 1000 are radially spaced from and parallel to a central axis in the pump unit.

The upper end of each cylinder 1202 is disposed in the bottom opening of a top clamp 1206, which may be made of polypropylene. The lower end of each cylinder 1202 is disposed in the top opening of a bottom clamp 1212, which also may be made of polypropylene. Gaskets 1204 are provided to seal the joints between cylinders 1202 and clamps 1206 and 1212. Shoulders on clamps 1206 and 1212 enable cylinder 1202 to be captured between top plate 1100 and bottom plate 1102. A pair of O-rings 1214 received within circumferential grooves 1216 in each piston 1200 form a seal between a piston 1200 and its cylinder 1202. The lower ends 1218 of pistons 1200 are secured to a flange 1104 which, when raised and lowered by a mechanism driven by motor 1106, drives pistons 1200 upwardly and downwardly, respectively, within cylinders 1102. The pressure or vacuum created by axial motion of pistons 1200 within cylinders 1202 expels fluid from or draws fluid into the spaces above pistons 1200.

The upper end 1226 of clamp 1206 engages a distributor 1208 having three openings 1230 adapted to receive fittings 1210 coupled to the ends of tubing lines. Openings 1230 communicate via passages 1234 (FIGS. 13a and 13b) with a common space in distributor 1208. Clamp 1206 and distributor 1208 provide a closure for cylinder 1202. Their inner surfaces, together with the inner surface of cylinder 1202 and the surfaces of piston 1200 above upper O-ring 1214, define a chamber having a volume that changes with axial movement of piston 1200 within cylinder 1202. Apertures defined by passages 1234 allow pumped fluid to be delivered into or withdrawn from tubing lines coupled to fittings 1210. Thus, distributor 1208 allows fluid to be pumped to or from a line 102 to a sample collector, a line 106 to a dissolution unit, and a line 110 to a replacement medium vessel.

Figure 13A:
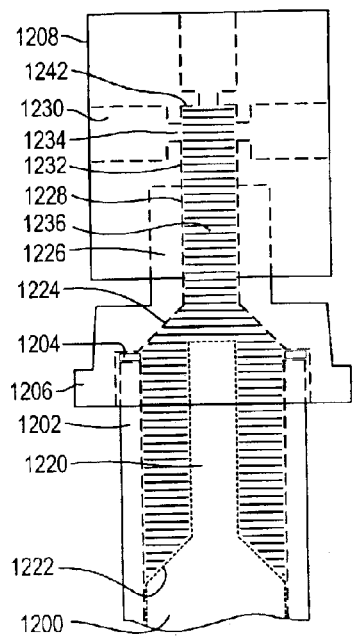
FIG. 13 is a detailed view of a portion of the syringe pump of FIG. 10.
Figure 13B:
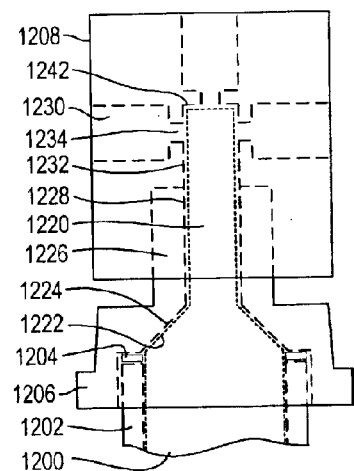

FIG. 13*a* is an enlarged detailed view of the upper end of the syringe pump of FIGS. 10–12 with the piston partially withdrawn from the cylinder, and FIG. 13*b* is a corresponding view with the piston fully advanced into the cylinder. It is desirable to minimize the residual fluid volume remaining in a pump when it has delivered as much fluid as it can. To this end, piston 1200 includes a surface having substantially the shape of the chamber-defining surfaces of the closure. In particular, frusto-conical surface 1222 and the surface of reduced-diameter cylindrical portion 1220 of piston 1200 have substantially the same shape as surfaces 1224 and 1228 of clamp 1206 and surfaces 1232 and 1242 of distributor 1208. Thus, chamber 1236 in FIG. 13*a* (indicated by horizontal hatching) is substantially eliminated when piston 1200 is fully advanced, and portions of the piston surface are closely adjacent the apertures in passages 1234.

Figure 14:
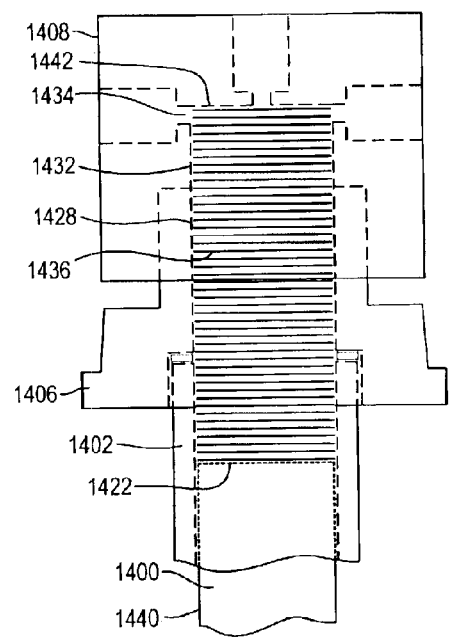
FIG. 14 is a detailed view of a portion of another syringe pump.

FIG. 14 is a detailed view of a portion of a syringe pump analogous to that of FIG. 13*a* illustrating that a conventional cylindrically-shaped piston can also be used in a pump structure that minimizes residual volume. Piston 1400 includes a surface having substantially the shape of the chamber-defining surfaces of the closure of cylinder 1402 formed by clamp 1406 and distributor 1408. In particular, the surface defined by face 1422 and a portion of cylindrical surface 1440 of piston 1400 has substantially the same shape as the closure surface defined by cylindrical surface 1428 of clamp 1406, cylindrical surface 1432 of distributor 1408, and circular surface 1442 of distributor 1408. Thus, chamber 1436 (indicated by horizontal hatching) is substantially eliminated when piston 1400 is fully advanced, and portions of the surface of piston 1400 are closely adjacent the apertures in passages 1434 of distributor 1408.

The pistons in both FIG. 13 and FIG. 14 extend past the end of the cylinders when fully advanced. However, a syringe pump could achieve low residual volume without that property if the apertures were disposed in a closure providing a chamber-defining surface in the plane of the upper end of the cylinder.

The pump unit includes three valve arrays 1120, two of which are visible in FIG. 11. Each valve array 1120 receives one tubing line from each distributor 1208. Valve arrays 1120 are pinch valves which, when actuated, press upon tubing lines to stop flow.

In accordance with embodiments of another aspect of the invention, the sampler includes a leak detector. The leak detector preferably includes a leak sensor having electrical properties that change in response to the presence of fluid, and an electronic circuit coupled to the leak sensor that generates a leak-indicating signal when the electrical properties of the leak sensor correspond to the presence of spilled fluid. In a preferred embodiment, the leak sensor includes a pair of spaced conductors, and the leak detector includes electronic circuitry coupled to the conductors that is responsive to the electrical properties of the material adjacent the conductors. The presence of distributors and fluid couplings in the region above plate 1100 make it susceptible to leaks, and a leak sensor may desirably be disposed in that region.

Figure 15:
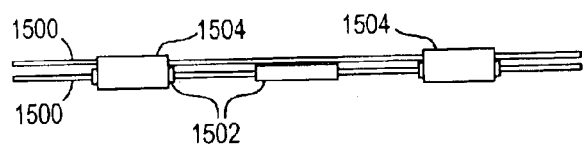
FIG. 15 is a plan view of a leak sensor in accordance with the invention.

FIG. 15 is a plan view of an embodiment of a leak sensor in accordance with the invention. A pair of wires 1500 are spaced apart by tubular insulators 1502 that surround one of the wires, and are held adjacent each other to form a unitary sensor assembly by insulators 1504. Wires 1500 may be made of stainless steel, and insulators 1502 and 1504 may be made of Teflon®. Fluid which bridges wires 1500 will increase the electrical conductance and/or capacitance between the wires, and many circuits are known for detecting such changes. The structure of the leak sensor allows it to be flexible, which enables a length of leak sensor to be "snaked" around on a surface such as upper surface 1110 of top plate 1100 to permit small leaks to be detected over most of the surface.

As has been described, performing a dissolution test requires head 506 of sample collector 500 to move in the direction of arrow 504 to a particular position, for instance, to deliver samples withdrawn at a particular time to the correct row of collection receptacles in rack 508. In addition, base 502 may contain a row of receptacles for receiving excess fluid withdrawn from dissolution vessels so that the fluid can be recycled, or for receiving clean test solution used to wash the lines between samples. Base 502 may also contain a common rinse fluid receptacle in which needles may be dipped to rinse them in between samples. Such media recycling and rinse fluid receptacles would be located in the area of base 502 beneath head 506 in the position shown in FIG. 5, which is referred to as the home position.

A dissolution test method includes specification, among other parameters, of the time intervals at which samples are to be withdrawn from a dissolution vessel. Parameters of a test method may be entered into a memory in controller 230 via a local data entry device such as a keypad or via a communication channel and, for repeated use, may be stored in and recalled from a nonvolatile memory. In addition to the time intervals at which samples are to be withdrawn from a dissolution vessel, such parameters may include the volume of test solution to be withdrawn, the volume of withdrawn test solution to be delivered as a sample, the volume of fluid to be used in flushing the lines, whether test solution is to be replaced or recycled, whether samples are to be transferred automatically from collection receptacles to an analytical instrument, and times and fluid flow rates at which these processes are to take place.

Parameters may be entered into a controller for a test method which the sampler is unable to execute, for example, due to insufficient time to complete one or more tasks within the time allotted for them. For instance, head 506 will be required to be at particular positions with respect to the collection receptacles in rack 508 within certain ranges of times with respect to withdrawal of a sample in order to perform particular tasks in connection with the sample, such as needle rinsing, sample delivery, and flushing of the lines. Movement of the head from one position to another takes time, the amount of which varies depending on the mechanical capabilities of the sample collector and the distance the head must move. The time necessary for a fluid withdrawal or delivery step depends on the volume and flow rate for the step. The aggregate time necessary for the sampler to move and pump in performing a task may conflict with the time requirements of the test method. In accordance with embodiments of another aspect of the invention, a sampler controller analyzes a test method and determines whether the sampler can operate in accordance with the test method. If not, the controller precludes the sampler from attempting to perform the test method, and may generate an output so indicating; if so, the controller controls the sampler to perform the test method. This process helps avoid commencing a test that cannot be completed according to the specified test method.

Although the time intervals at which samples are withdrawn from the dissolution vessels must be maintained, other parameters of a test method can be varied, such as the time at which samples are delivered to collection receptacles, and the time of ancillary steps such as flushing. For instance, when a sample is withdrawn from a dissolution vessel into the chamber of a syringe pump, the chamber provides temporary storage of the sample. The sample need not be delivered to a collection receptacle immediately; delivery can be delayed, so long as the length of the delay leaves sufficient time for all required tasks to be performed prior to the next sample withdrawal time. It may be possible to vary parameters of a test method such as sample delivery time and flushing time so that the varied test method can be performed by the sampler while maintaining the required sampling intervals.

In a preferred embodiment, if the controller determines that a test method cannot be performed by the sampler, the controller commences varying parameters of the test method, other than the time intervals at which samples are to be taken, in order to determine if a test method so varied can be performed by the sampler. If the controller determines that a test method so varied can be performed by the sampler, the controller controls the sampler to perform the varied test method. If the controller cannot determine any varied test method that can be performed by the sampler, the controller precludes the sampler from attempting to perform the test method, and may generate an output so indicating.

Independently operable pump units makes it mechanically possible for sample collector 500 to operate with dissolution units to perform tests concurrently using two different test methods. However, a particular pair of test methods cannot necessarily be performed concurrently, because they might impose conflicting requirements on the sampler, for instance, as to the position of head 506.

Figure 16:
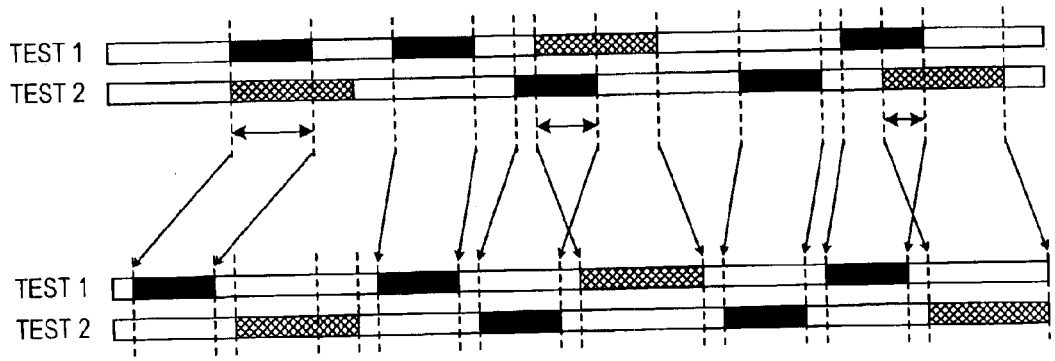
FIG. 16 is a timing diagram illustrating a conflicting pair of test methods which would require a sampler head to be in different positions simultaneously, and a variation of test method parameters which avoids the conflict.

FIG. 16 is a timing diagram illustrating a pair of test methods which would require a sampler head to be in different positions simultaneously. In a flushing step, the head must move to the home position and deliver the fluid used to flush the lines. In a sample delivery step, the head must move to position the needles over the appropriate row of collection receptacles and deliver the sample; often, prior to delivering a sample, the head must move to the home position and discharge excess test solution withdrawn from the dissolution vessels. Tasks such as flushing and sample delivery can impose conflicting requirements on head position.

FIG. 16 shows time lines indicating head position requirement for two tests employing different test methods. Black portions of the time lines indicate flushing steps when the head is required to be at the home position, and hatched portions indicate sample delivery steps when the head is required to be at a particular collection receptacle row. In the top pair of time lines, three periods of conflict exist, which are indicated by horizontal arrows. However, it may be possible to advance or delay the time at which certain tasks are performed. Although the time intervals at which samples are withdrawn from the dissolution vessels must be maintained, other parameters of a test method can be varied, such as the time at which samples are delivered to collection receptacles, and the time of ancillary steps such as flushing. It may be possible to vary such parameters for one or both tests, including the relative timing of the sampling, so that the varied test methods can be performed concurrently, while maintaining the required sampling intervals for both tests.

The bottom pair of timelines illustrates variation of the parameters of the test methods of from the upper pair of time lines to avoid requiring a sampler head to be in different positions simultaneously. The diagonal arrows indicate the adjustment of the times of certain flushing and delivery tasks. As varied, the test methods can be performed concurrently. It should be noted that the variations illustrated in FIG. 16 do not represent variations in the sampling interval of either test.

As discussed above, the design of a sampler establishes certain performance parameters such as how long it will take a head to move from one position to another, and how long it takes to perform a given task at a position. In accordance with embodiments of one aspect of the invention, a controller for a sampler determines whether a pair of test methods can be performed concurrently by the sampler. The determination may be based on the parameters of the sampler and of the test methods. If not, the controller precludes the sampler from attempting to perform both test methods concurrently, and may generate an output so indicating; if so, the controller controls the sampler to perform the test methods concurrently. Preferably, prior to determining if a conflict exists between a pair of test methods, the controller evaluates each test method as described above to determine whether the sampler can perform it.

In a preferred embodiment, if a pair of test methods cannot be performed concurrently by the sampler, the sampler commences varying parameters of one or both test methods, other than the time intervals at which samples are to be taken, in order to determine if a pair of test methods so varied can be performed concurrently by the sampler. If the controller determines that a pair of test methods so varied can be performed concurrently by the sampler, the controller controls the sampler to perform the varied test methods concurrently. If the controller cannot determine any varied pair of test methods that can be performed concurrently by the sampler, the controller precludes the sampler from attempting to perform both test methods concurrently, and may generate an output so indicating.

If two dissolution tests are to be performed concurrently, it may be desirable to start them at different times, and they may be completed at different times. To facilitate concurrent dissolution testing, instead of a single rack for receiving collection receptacles, a sample collector might accommodate a pair of separately removable racks. For instance, two racks, each half the width of rack 508 shown in FIG. 5, might be separately insertable into and removable from base 502. Collection receptacles in one of the removable racks might receive samples from needle head 700A withdrawn in a first dissolution test, and collection receptacles in the other removable rack might receive samples from needle head 700B withdrawn in a second dissolution test. When collection of samples in one of the tests is completed, the rack containing those samples can be removed for analysis and replaced by another rack to enable another test to be started.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A sampler adapted to operate concurrently in accordance with a first test method and a second test method different from the first test method, the first test method including withdrawing samples of fluid from each of a first set of vessels at a first set of time intervals and delivering the samples to a corresponding first set of collection receptacles, and the second test method including withdrawing samples of fluid from each of a second set of vessels at a second set of time intervals and delivering the samples to a corresponding second set of collection receptacles;

wherein the sampler includes a controller and a head having fluid delivery apparatus, the head and the collection receptacles being relatively positionable in response to signals from the controller to enable samples to be delivered to specified collection receptacles.

2. The invention of claim 1, wherein the sampler includes a first pump unit adapted to withdraw samples of fluid from the first set of vessels and a second pump unit adapted to withdraw samples of fluid from the second set of vessels, the pump units being independently operable in response to signals from the controller.

3. The invention of claim 1, wherein the controller determines whether operating the sampler concurrently in accordance with the first and second test methods would require the head and the collection receptacles to be in two different relative positions simultaneously.

4. The invention of claim 3, wherein the controller operates the sampler concurrently in accordance with the first and second test methods in response to a determination that such operation would not require the head and the collection receptacles to be in two different relative positions simultaneously.

5. The invention of claim 3, wherein the controller precludes operating the sampler concurrently in accordance with the first and second test methods in response to a determination that such operation would require the head and the collection receptacles to be in two different relative positions simultaneously.

6. The invention of claim 3 wherein, in response to a determination that operating the sampler concurrently in accordance with the first and second test methods would require the head and the collection receptacles to be in two different relative positions simultaneously, the controller determines whether varying one or more parameters of the first test method and/or the second test method, other than the time intervals at which samples are to be withdrawn, would enable operating the sampler concurrently without requiring the head and the collection receptacles to be in two different relative positions simultaneously.

7. The invention of claim 6, wherein the controller operates the sampler concurrently in accordance with the first and second test methods with varied parameters, in response to a determination that such operation would not require the head and the collection receptacles to be in two different relative positions simultaneously.

8. The invention of claim 6, wherein the controller precludes operating the sampler concurrently in accordance with the first and second test methods with varied parameters in response to a determination that such operation would require the head and the collection receptacles to be in two different relative positions simultaneously.

9. The invention of claim 6, wherein the parameters include the time at which a sample is delivered to a collection receptacle.

10. The invention of claim 6, wherein the parameters include the time at which tubing lines that provided to convey samples are flushed.

11. The invention of claim 1, wherein the head includes first fluid delivery apparatus adapted to deliver samples of fluid from the first set of vessels and second fluid delivery apparatus adapted to deliver samples of fluid from the second set of vessels, the first and second fluid delivery apparatus being independently operable in response to signals from the controller.

12. A method of operating a sampler, the sampler including collection receptacles and a head having fluid delivery apparatus, the head and the collection receptacles being relatively positionable to enable samples of fluid withdrawn from each of a set of vessels in accordance with a test method to be delivered to a corresponding set of collection receptacles, comprising:

determining whether operating the sampler concurrently in accordance with a first test method and a second test method different from the first test method would require the head and the collection receptacles to be in two different relative positions simultaneously, the first test method including withdrawing samples of fluid from each of a first set of vessels at a first set of time intervals and delivering the samples to a corresponding first set of collection receptacles, the second test method including withdrawing samples of fluid from each of a second set of vessels at a second set of time intervals and delivering the samples to a corresponding second set of collection receptacles; and controlling operation of the sampler in response to the determination.

13. The invention of claim 12, wherein controlling operation of the sampler includes controlling the operation of a plurality of independently operable pump units.

14. The invention of claim 12, wherein controlling operation of the sampler includes operating the sampler concurrently in accordance with the first and second test methods in response to a determination that such operation would not require the head and the collection receptacles to be in two different relative positions simultaneously.

15. The invention of claim 12, wherein controlling operation of the sampler includes precluding operation of the sampler concurrently in accordance with the first and second test methods in response to a determination that such operation would require the head and the collection receptacles to be in two different relative positions simultaneously.

16. The invention of claim 12 further comprising, in response to a determination that operating the sampler concurrently in accordance with the first and second test methods would require the head and the collection receptacles to be in two different relative positions simultaneously, determining whether varying one or more parameters of the first test method and/or the second test method, other than the time intervals at which samples are to be withdrawn, would enable operating the sampler concurrently without requiring the head and the collection receptacles to be in two different relative positions simultaneously.

17. The invention of claim 16, further comprising operating the sampler concurrently in accordance with the first and second test methods with varied parameters, in response to a determination that such operation would not require the head and the collection receptacles to be in two different relative positions simultaneously.

18. The invention of claim 16, further comprising precluding operation of the sampler concurrently in accordance with the first and second test methods with varied parameters, in response to a determination that such operation would require the head and the collection receptacles to be in two different relative positions simultaneously.

19. The invention of claim 16, wherein the parameters include the time at which a sample is delivered to a collection receptacle.

20. The invention of claim 16, wherein the parameters include the time at which tubing lines that are provided to convey samples are flushed.

21. A sampler comprising:
   a head having one or more fluid delivery devices, each device adapted to deliver one or more samples of fluid to one or more selected collection receptacles; and
   a controller adapted to control relative positioning of the head and the one or more selected collection receptacles to enable the one or more samples to be delivered to the one or more selected collection receptacles, wherein:
   the controller is adapted to operate concurrently in accordance with a first test method and a second test method different from the first test method;
   the first test method includes withdrawing samples of fluid from each of a first set of vessels at a first set of time intervals and the one or more fluid delivery devices delivering the samples to a corresponding first set of collection receptacles; and
   the second test method includes withdrawing samples of fluid from each of a second set of vessels at a second set of time intervals and the one or more fluid delivery devices delivering the samples to a corresponding second set of collection receptacles.

22. The invention of claim 21, wherein the sampler includes first pump unit adapted to withdraw samples of fluid from the first set of vessels and a second pump unit adapted to withdraw samples of fluid from the second set of vessels, the pump units being independently operable in response to signals from the controller.

23. The invention of claim 21, wherein the controller determines whether operating the sampler concurrently in accordance with the first and second test methods would require the head and the collection receptacles to be in two different relative positions simutaneously.

24. The invention of claim 23, wherein the controller operates the sampler concurrently in accordance with the first and second test methods in response to a determination that such operation would not require the head and the collection receptacles to be in two different relative positions simultaneously.

25. The invention of claim 23, wherein the controller precludes operating the sampler concurrently in accordance with the first and second test methods in response to a determination that such operation would require the head and the collection receptacles to be in two different relative positions simultaneously.

26. The invention of claim 23, wherein, in response to a determination that operating the sampler concurrently in accordance with the first and second test methods would require the head and the collection receptacles to be in two different relative positions simultaneously, the controller determines whether varying one or more parameters of the first test method and/or the second test method, other than the time intervals at which samples are to be withdrawn, would enable operating the sampler concurrently without requiring the head and the collection receptacles to be in two different relative positions simultaneously.

27. The invention of claim 26, wherein the controller operates the sampler concurrently in accordance with the first and second test methods with varied parameters, in response to a determination that such operation would not require the head an the collection receptacles to be in two different relative positions simultaneously.

28. The invention of claim 26, wherein the controller precludes operating the sampler concurrently in accordance with the first and second test methods with varied parameters in response to a determination that such operation would require the head and the collection receptacles to be in two different relative positions simultaneously.

29. The invention of claim 26, wherein the parameters include the time at which a sample is delivered to a collection receptacle.

30. The invention of claim 26, wherein the parameters include the time at which tubing lines that provided to convey samples are flushed.

31. The invention of claim 21, wherein the one or more fluid delivery devices include a first fluid delivery device adapted to deliver samples of fluid from the first set of vessels and a second fluid delivery device adapted to deliver samples of fluid from the second set of vessels, the first and second fluid delivery devices being independently operable in response to signals from the controller.

* * * * *